(12) United States Patent
Sliger

(10) Patent No.: US 8,376,103 B1
(45) Date of Patent: Feb. 19, 2013

(54) CABLE MANAGEMENT SYSTEM

(75) Inventor: Bradley J. Sliger, Seattle, WA (US)

(73) Assignee: SonoSite, Inc., Bothell, WA (US)

( * ) Notice: Subject to any disclaimer, the term of this patent is extended or adjusted under 35 U.S.C. 154(b) by 342 days.

(21) Appl. No.: 12/704,469

(22) Filed: Feb. 11, 2010

(51) Int. Cl.
*H02G 11/02* (2006.01)

(52) U.S. Cl. ................. 191/12.4; 191/12.2 R; 242/378.4

(58) Field of Classification Search ............. 191/12.2 R, 191/12 R, 12.4, 12.2 A; 242/378, 378.4; 254/393, 395, 396
See application file for complete search history.

(56) References Cited

U.S. PATENT DOCUMENTS

| | | | | |
|---|---|---|---|---|
| 3,182,139 | A * | 5/1965 | Meletti | 191/12.4 |
| 3,657,491 | A * | 4/1972 | Ryder et al. | 191/12.2 R |
| 4,114,736 | A * | 9/1978 | Scherenberg | 191/12.4 |
| 4,744,763 | A * | 5/1988 | Suzuki et al. | 439/15 |
| 5,094,396 | A * | 3/1992 | Burke | 242/378.2 |
| 5,535,960 | A * | 7/1996 | Skowronski et al. | 242/378.4 |
| 6,019,304 | A * | 2/2000 | Skowronski et al. | 242/373 |
| 6,372,988 | B1 * | 4/2002 | Burke et al. | 174/69 |
| 7,172,150 | B1 * | 2/2007 | Hutchison et al. | 242/375.2 |
| 2004/0200920 | A1 * | 10/2004 | Wei | 242/378.4 |
| 2005/0236243 | A1 * | 10/2005 | Huang | 191/12.4 |
| 2006/0186248 | A1 * | 8/2006 | Liao | 242/378 |
| 2010/0072013 | A1 * | 3/2010 | Carlucci | 191/12.4 |
| 2010/0096486 | A1 * | 4/2010 | Yang | 242/371 |
| 2010/0327099 | A1 * | 12/2010 | Kuo | 242/378 |

OTHER PUBLICATIONS

Retractable Drop Light Reel 15M Cable, Tradequip Products Online Catalog, http://www.tradequip.com.au/products/products.php?code=TQ1066, Download date Feb. 9, 2010, 2 pages.

* cited by examiner

*Primary Examiner* — Jason C Smith

(57) ABSTRACT

A cable management system for use with electrical devices, such as, for example, a ultrasound imaging system, is provided comprising a rotatable reel coupled to an end of each of an elongated flexible circuit member and an elongated cable. Each of a plurality of wires of the cable is electrically coupled to a respective conductor of the flexible circuit member to create separate conductive paths or signal channels. The cable management system is configured such that, as the cable moves from a generally retracted configuration in which a majority of the cable is wound about the reel to a generally extended configuration, the flexible circuit member simultaneously contracts about the reel. As a corollary, the flexible circuit member relaxes or unwinds as the cable moves from the extended configuration towards the retracted configuration.

18 Claims, 5 Drawing Sheets

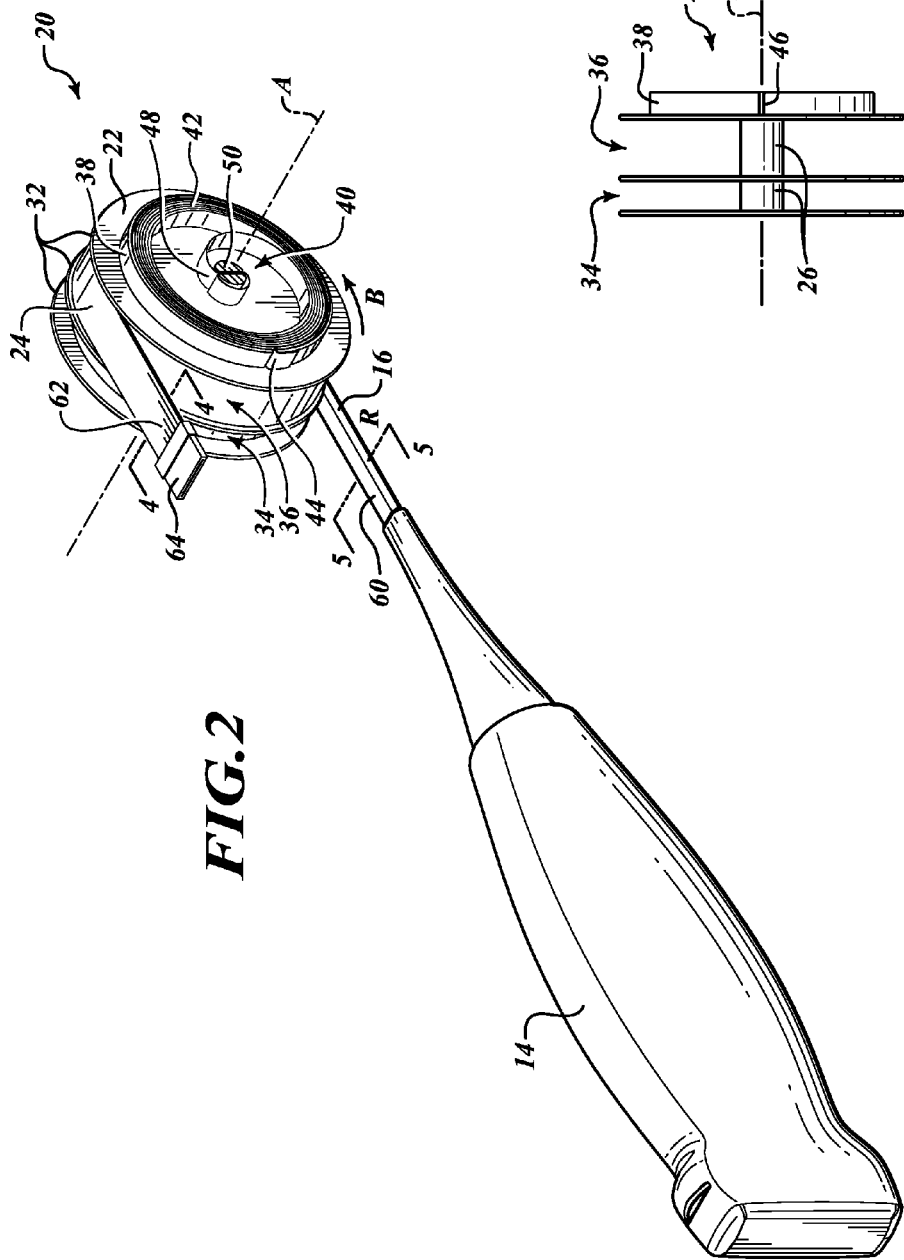

CABLE MANAGEMENT SYSTEM

BACKGROUND

1. Technical Field

This application relates to cable management systems, and more particularly to cable management systems suitable for selectively extending and retracting a cable from an electronic device, such as, for example, an ultrasound diagnostic imaging system.

2. Description of the Related Art

Various devices for managing cables or cords of electronic equipment have been developed ranging from simple bundling devices, such as cable ties, to more complex retraction devices, such as the cord retractor device shown and described in U.S. Pat. No. 4,114,736. Cord retraction devices are typically used to manage excess cord lengths in a manner that is more efficient and aesthetically pleasing than bundling devices. Some cord retraction devices enable a user to operate an electrical tool, appliance or other apparatus remotely from a power source via an extended power cord, and then reel in the cord for storage. Such power cord retraction devices typically include brush contact mechanisms for maintaining a conductive path from a power outlet to the electrical tool, appliance or other apparatus as the power cord is extended and retracted. For example, the cord retractor shown and described in U.S. Pat. No. 4,114,736 includes a brush contact mechanism in the form of electrically conductive rings secured to a rotatable drum that correspond to each of a live wire and neutral wire of a power cord and which are aligned with respective contacts on a base portion of the cord retractor. The contacts of the base portion are biased towards the conductive rings to maintain contact therewith as the drum rotates, and thereby maintain a conductive path. Cord retraction devices having such brush contact mechanisms are generally used for applications wherein only a few conductive paths are provided and for providing electrical power where appreciable signal degradation through the brush contacts is of no concern.

Applicant's new cable management systems are particularly well suited for extending and retracting electrical cables for a broader range of applications.

BRIEF SUMMARY

The cable management systems described herein provide for the selective extension and retraction of a cable in a manner particularly adapted to maintain high quality electrical signals over a multitude of separate conductive paths or signal channels, such as, for example, twenty or more separate signal channels.

A cable management system may be summarized as including an elongated flexible circuit member including a flexible base substrate and a plurality of conductors; and an elongated cable including a plurality of wires, at least one of the wires of the cable electrically coupled to a conductor of the elongated flexible circuit member, the cable movable between a generally retracted configuration and a generally extended configuration, and wherein, when the cable moves towards the generally extended configuration, the flexible circuit member contracts about a central axis with an end of the flexible circuit member remaining substantially fixed relative to the central axis. The cable management system may further include a shaft physically coupled to an end of the cable and an end of the flexible circuit member, the shaft configured to rotate about the central axis as the cable moves between the generally extended and generally retracted configurations.

A cable management system may also be summarized as including a reel rotatable about a central axis, the reel including a central shaft; an elongated flexible circuit member coupled at one end to the central shaft of the reel, the flexible circuit member including a flexible base substrate and a plurality of conductors; and an elongated cable including a plurality of wires coupled at one end to the central shaft of the reel, at least one of the wires of the cable electrically coupled to a conductor of the flexible circuit member, and wherein the cable is movable between a generally retracted configuration and a generally extended configuration, the flexible circuit member winding about the reel when the cable moves towards the generally extended configuration and unwinding from the reel when the cable moves towards the generally retracted configuration.

The cable management system may further include a spring to bias the cable towards the generally retracted configuration. The spring may have a first end and a second end, the first end of the spring fixed relative to the central axis and the second end of the spring coupled to the reel to bias the cable towards the generally retracted configuration. The reel may include a first channel sized to receive the majority of the cable in the generally retracted configuration and a second channel sized to receive a majority of the flexible circuit member in each of the generally retracted and generally extended configurations.

A cable management system for an ultrasound instrument may be summarized as including a reel rotatable about a central axis, the reel including a central shaft; an elongated flexible circuit member having a flexible base substrate and a plurality of conductors, a first end of the flexible circuit member coupled to the central shaft of the reel to rotate in unison therewith; an elongated cable having a plurality of wires, a first end of the cable coupled to the central shaft of the reel to rotate in unison therewith and each of the wires electrically coupled to a respective conductor of the flexible circuit member; and a transducer unit communicatively coupled to a second end of the cable, the transducer unit movable between a retracted configuration and an extended configuration, the flexible circuit member winding about the central shaft of the reel as the transducer unit moves away from the retracted configuration. The cable management system may further include an electrical connector coupled to a second end of the flexible circuit member to electrically connect the conductors of the flexible circuit member to a control and display unit of the ultrasound diagnostic instrument, the electrical connector being substantially fixed relative to the central axis of the reel when connected to the control and display unit.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles may not be drawn to scale, and some of these elements may be arbitrarily enlarged and positioned to improve drawing legibility.

FIG. 2 is an isometric view of a cable management system, according to one illustrated embodiment.

FIG. 3 is a front elevational view of a reel of the cable management system of FIG. 2.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with cord retractor devices, electrical cables and electrical connectors have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

Figure 1:
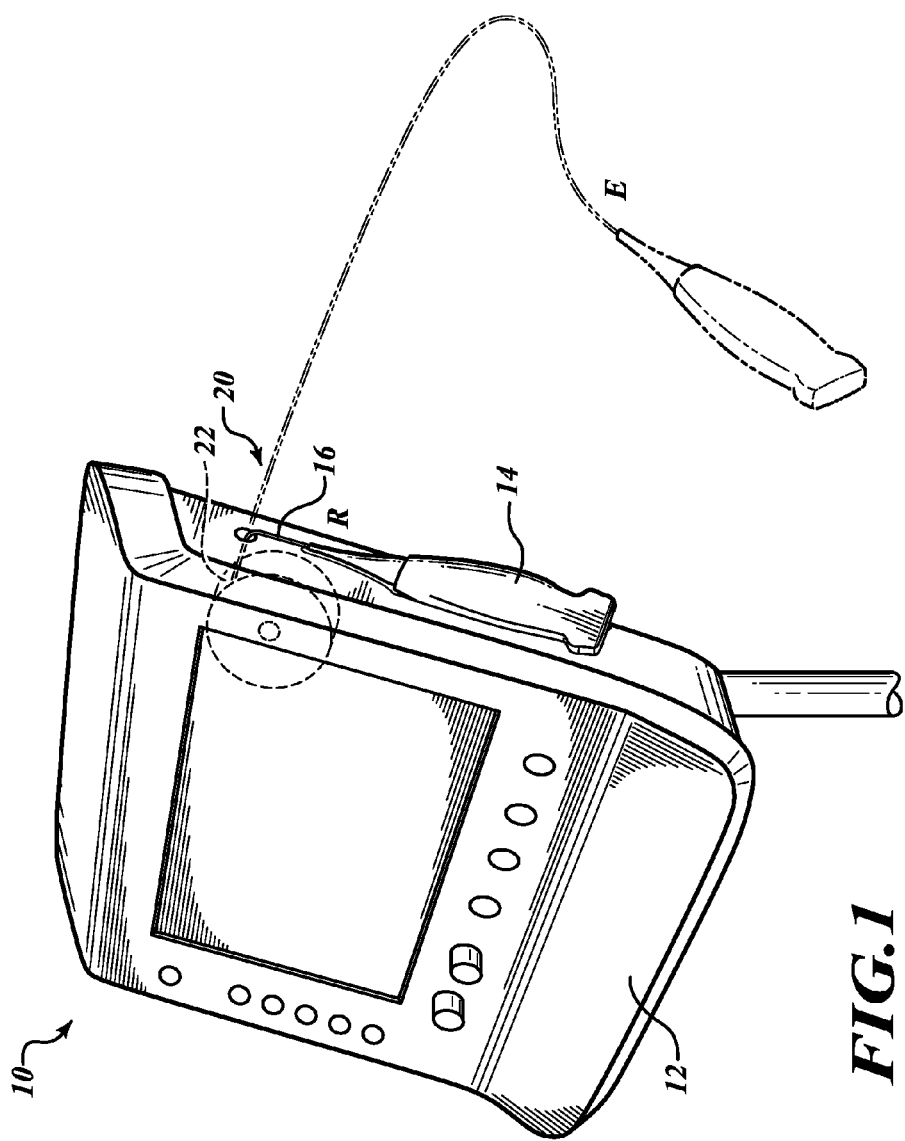
FIG. 1 is an isometric view of an ultrasound diagnostic imaging system having a control and display unit and a transducer unit coupled thereto via a cable management system, according to one illustrated embodiment.

FIG. 1 shows an ultrasound diagnostic imaging system 10 having a control and display unit 12 and a transducer unit 14 coupled thereto via a cable 16 of a cable management system 20, according one embodiment.

The cable management system 20 enables a user to selectively extend and retract the cable 16 attached to the transducer unit 14 from the control and display unit 12. The cable 16 may be selectively extended and retracted from the control and display unit 12 between a retracted configuration R in which the cable 16 is wound about a rotatable reel 22 of the cable management system 20 and an extended configuration E (shown in broken line) in which the cable 16 is unwound from the reel 22.

The cable management system 20 may advantageously enable a user to selectively extend and retract a cable 16 having a multitude of wires in a manner that can maintain high quality electrical signals. More particularly, the cable 16 may include a plurality of wires that are electrically coupled to a printed circuit board or other processing device within the control and display unit 12 without intermediate brush contact mechanisms. In this manner, continuous uninterrupted conductive paths or signal channels may be provided with relatively less resistance than would otherwise be expected of cable systems utilizing brush contacts. Consequently, higher quality signals may be maintained which is advantageous for applications where signal integrity is of particular concern, such as, for example, an ultrasound diagnostic imaging system 10 in which image quality is strongly dependent on signal integrity.

Further, because embodiments of the cable management systems 20 described herein do not rely on concentrically aligned contact rings typical of brush contact mechanisms, the cable management systems 20 are particularly suited for scaling the number of conductive paths or signal channels that may be maintained through the cable management system 20. For example, in some embodiments, the cable 16 may take the form of a signal cable that includes twenty or more wires for transmitting various channels of data. The cable management system 20 is thus particularly suitable for use in applications requiring many distinct channels of information, such as, for example, an ultrasound diagnostic imaging system 10 which typically includes a plurality of signal channels corresponding to transducers retained in the transducer unit 14.

FIGS. 2 and 3 show the cable management system 20 in more detail. The cable management system 20 includes the reel 22, the cable 16 and an elongated flexible circuit member 24. The reel 22 is mounted for rotation about a central axis A. A width and/or diameter of the reel 22 may be sized in accordance with a desired capacity (i.e., the number of signal channels provided) of the cable management system 20 to accommodate the cross-sectional dimensions of the cable 16 and the flexible circuit member 24 and/or extended length of the cable 16.

The reel 22 may include a central shaft 26 about which each of the cable 16 and the flexible circuit member 24 may wind and unwind during operation. A first end 28 (FIGS. 6 and 7) of the cable 16 and a first end 30 (FIGS. 6 and 7) of the flexible circuit member 24 are each physically coupled or otherwise secured to the central shaft 26 such that as the central shaft 26 rotates each of the first end 28 of the cable 16 and first end 30 of the flexible circuit member 24 rotate in unison therewith. The cable 16 and the flexible circuit member 24 may be physically coupled or secured to the central shaft 26 using various connection structures, such as, for example, connectors, clamps, crimps, clips, snaps, straps, detents or the like.

With continued reference to FIGS. 2 and 3, the reel 22 may include a set of radially extending walls 32 that form a pair of channels, namely cable channel 34 and flexible circuit member channel 36. The channels 34, 36 are respectively sized to receive the cable 16 and the flexible circuit member 24 of the cable management system 20. The channels 34, 36 substantially confine side-to-side or lateral movement of the cable 16 and the flexible circuit member 24 during operation to prevent twisting or binding of the same. The reel 22 may further include a retaining wall 38 that projects from a side thereof to form a cavity 40. The cavity 40 may be sized to receive a biasing element such as a spiral torsion spring 42 coupled to bias the reel 22 in a rotational direction shown by the arrow labeled B. The spring 42 is shown coupled to the reel 22 via the engagement of a hooked portion at a first end 44 of the spring 42 with a catch feature 46 on the retaining wall 38 of the reel 22. Different attachment structures may be used. A second end 48 of the spring 42 is secured to a center pin 50 on which the reel 22 is rotatably supported. The center pin 50 remains fixed when the reel 22 is rotated during operation. In this manner, the spring 42 winds progressively tighter about the center axis A as the reel 22 rotates in response to extraction or extension of cable 16 from the control and display unit 12 (FIG. 1). Consequently, the spring 42 increasingly biases the reel 22 and hence cable 16 back towards the retracted configuration R (FIG. 1) as the cable 16 is extended.

Figure 4:
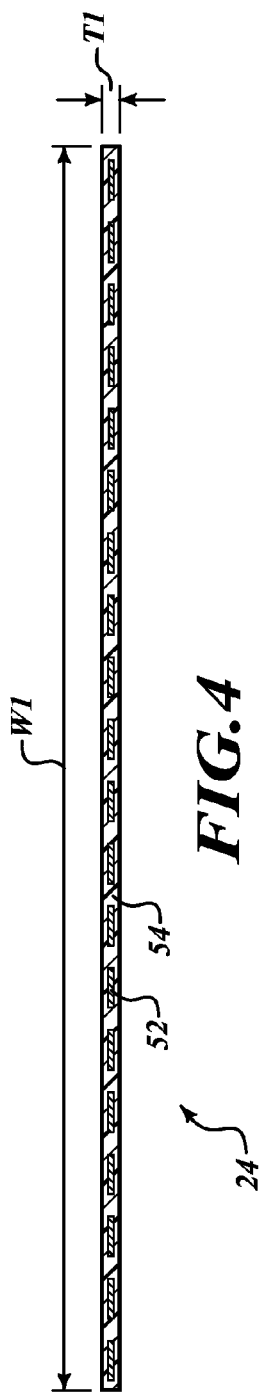
FIG. 4 is a cross-sectional view of the flexible circuit member of the cable management system of FIG. 2.
Figure 5:
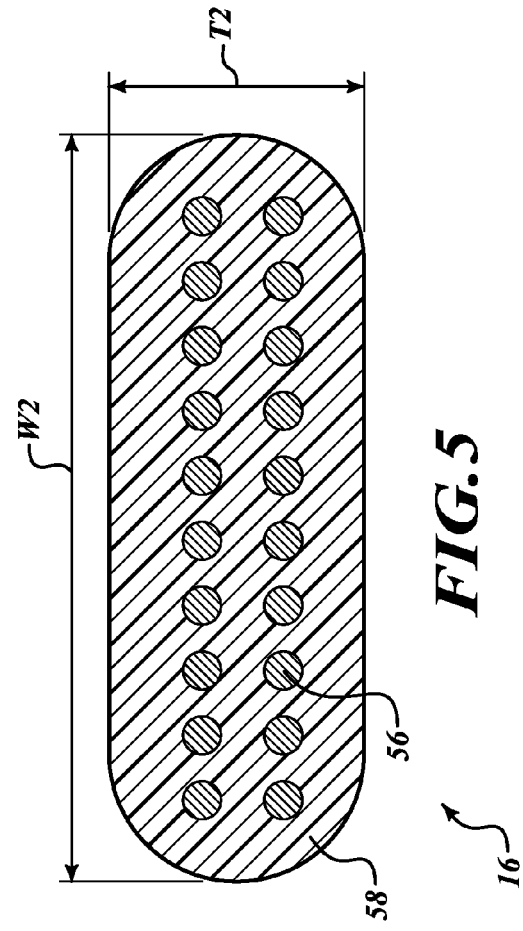
FIG. 5 is a cross-sectional view of the cable of the cable management system of FIG. 2.

FIGS. 4 and 5 illustrate a cross-section of the flexible circuit member 24 and a cross-section of the cable 16, respectively.

With reference to FIG. 4, the flexible circuit member 24 comprises a plurality of electrical conductors 52 (i.e., conductive paths) carried on one or more layers of an electrically insulating flexible base substrate 54. A variety of suitable electrically insulating materials for the base substrate 54 are commercially available, for instance FR-4 glass epoxy, polyimide (e.g., Kapton®), polyamide or polyester, and other materials used to produce printed circuit boards and flexible circuit substrates. The electrical conductors 52 may be formed by printing, depositing or otherwise providing any of a variety of electrically conductive materials (e.g., copper, gold, aluminum) on or within the base substrate 54 to create or form a continuous conductive path along a length of the flexible circuit member 24. Although the flexible circuit member 24 is illustrated as including a plurality of conductors 52 enclosed in a substantially homogeneous base substrate 54, the flexible circuit member 24 may include other components and/or may be formed as a layered or composite structure. For example, the flexible circuit member may comprise a number of layers of an electrically insulating material. The flexible circuit member 24 may further include an electrically conductive shield or grounding layer (not shown). As another example, the flexible circuit member 24 may act as or otherwise include a spring element integrally formed therewith that biases the flexible circuit member 24 radially outward with increasing force as the flexible circuit member 24 is wound about the central shaft 26 of the reel 22. Inclusion of the spring element in the flexible circuit member 24 may allow the spring 42 to be omitted. The spring element may provide shielding (e.g., RF shielding) and may increase the rigidity and resilience of the flexible circuit member 24.

The flexible circuit member 24 may be semi-rigid yet is flexible enough to enable winding and unwinding about the central shaft 26 during operation without appreciable permanent or plastic deformation. In some embodiments, the flexible circuit member 24 may be shaped to include a curvature or arc along the length thereof that corresponds approximately to the desired shape of the flexible circuit member 24 when in the retracted configuration R (FIG. 1) to reduce stress therein. The flexible circuit member 24 may have a substantially rectangular or oval profile defined by a nominal width W1 and a nominal thickness T1. The conductors 52 may be spaced equally along a common plane at any given cross-section within the flexible circuit member 24. Alternatively, the conductors 52 may be staggered, arranged in multiple rows or layers, and/or irregularly spaced. Further, although the flexible circuit member 24 is illustrated as having twenty separate conductors 52, the flexible circuit member 24 may include more or fewer conductors 52, such as, for example, one hundred or more conductors 52 or as few as two conductors 52.

With reference to FIG. 5, the cable 16 comprises a plurality of wires 56 surrounded by a cover 58 which electrically insulates the wires 56 from each other and other components. The wires 56 may comprise any of a variety of electrically conductive materials (e.g., copper, gold, aluminum), and may be solid wires or multi-strand wires which may, or may not, be braided. The cover 58 can take the form of any of a variety of dielectric materials, many of which are employed commercially as cable sheathes or covers. Although the cable 16 is illustrated as having a plurality of wires 56 enclosed in a substantially homogeneous material, the cable 16 may be formed to include other components and/or layers, such as, for example, a shielding layer. As another example, the cable 16 may be formed to include a plurality of separate individually insulated wires bundled together within an outer jacket.

The cable 16 may include flat outer surfaces to facilitate tight and consistent winding. Alternatively, the cable 16 may have other cross-sectional profiles, such as, for example, a generally circular cross-section. In any case, the cable 16 may be wound or unwound about the central shaft 26. In particular, the cable 16 may be wound to a fully retracted configuration R (FIG. 1) in which the vast majority of the cable 16 is wound about the central shaft 26 and retained within the cable channel 34. The cable 16 may be unwound to a fully extended configuration E (FIG. 1) in which the vast majority of the length of the cable 16 extends beyond the outer periphery of the reel 22 and the control and display unit 12. A cable 16 having a flat cross-sectional profile is particularly well suited to wind consistently and tightly in a relatively small form-factor or package.

The cable 16 may comprise a cross-sectional profile defined at least in part by a nominal width W2 and a nominal thickness T2. The wires 56 of the cable 16 may be spaced equally in a number of rows or in a common plane at any given cross-section. Alternatively, the conductors 52 may be staggered and/or irregularly spaced. The wires 56 of the cable 16 may be more robust than the conductors 52 of the flexible circuit member 24 to address durability concerns stemming from exposure to the environment. Further, although the cable 16 is illustrated as having twenty separate wires 56, the cable 16 may include more or fewer wires 56, such as, for example, one hundred or more wires 56 or as few as two wires 56.

In some embodiments, the nominal thickness T2 of the cable 16 is at least five times the nominal thickness T1 of the flexible circuit member 24. In other embodiments, the nominal thickness T2 of the cable 16 is at least ten times the nominal thickness T1 of the flexible circuit member 24. A larger ratio of the nominal thickness T2 of the cable 16 to the nominal thickness T1 of the flexible circuit member 24 advantageously provides relatively greater cable extension. For example, assuming the nominal thickness T2 of the cable 16 and a nominal thickness T1 of the flexible circuit member 24 are substantially equal, the cable 16 may not be wound to fill the entire diameter of the cable channel 34 of the reel 22 because if so, the corresponding flexible circuit member 24 of a length needed to enable full extension of the cable 16 would fill the flexible circuit member channel 36 of the reel 22 and leave no room or void for the flexible circuit member 24 to wind or contract into during operation. Accordingly, in such a construction, the cable 16 could only occupy a portion of the available space in the cable channel 34, thus reducing the available length for extension. Conversely, if the nominal thickness T1 of the flexible circuit member 24 is many times smaller than the nominal thickness T2 of the cable 16, then the entire cable channel 34 may be filled with cable 16 in the retracted configuration R while the vast majority of the flexible circuit member 24 is positioned in a relatively small peripheral portion of the flex circuit channel 34. Consequently, for a selected cable width, applications requiring longer cable extension lengths may have a relatively larger ratio of the nominal thickness T2 of the cable 16 to the nominal thickness T1 of the flexible circuit member 24 when compared to applications in which shorter cable extension lengths are acceptable or desirable, such as, for example, small portable equipment applications.

Figure 6:
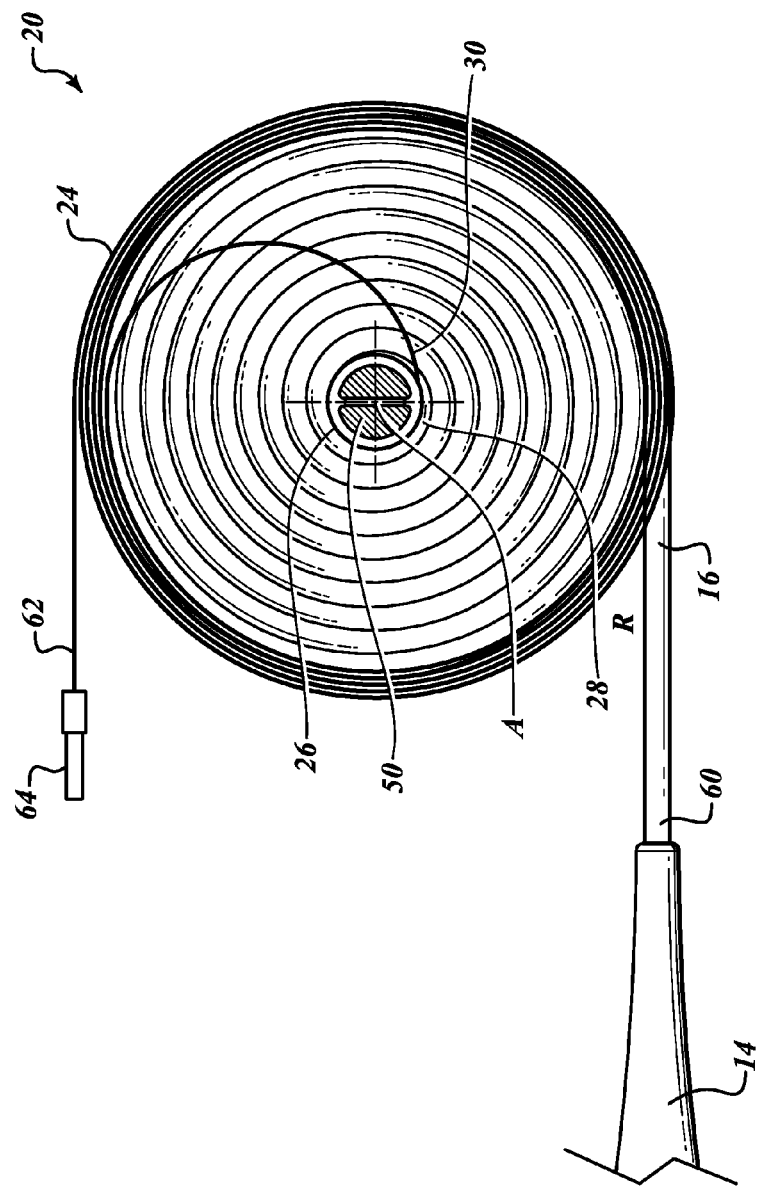
FIG. 6 is a schematic diagram showing a cable and a flexible circuit member of the cable management system of FIG. 2 in a cable retracted configuration.
Figure 7:
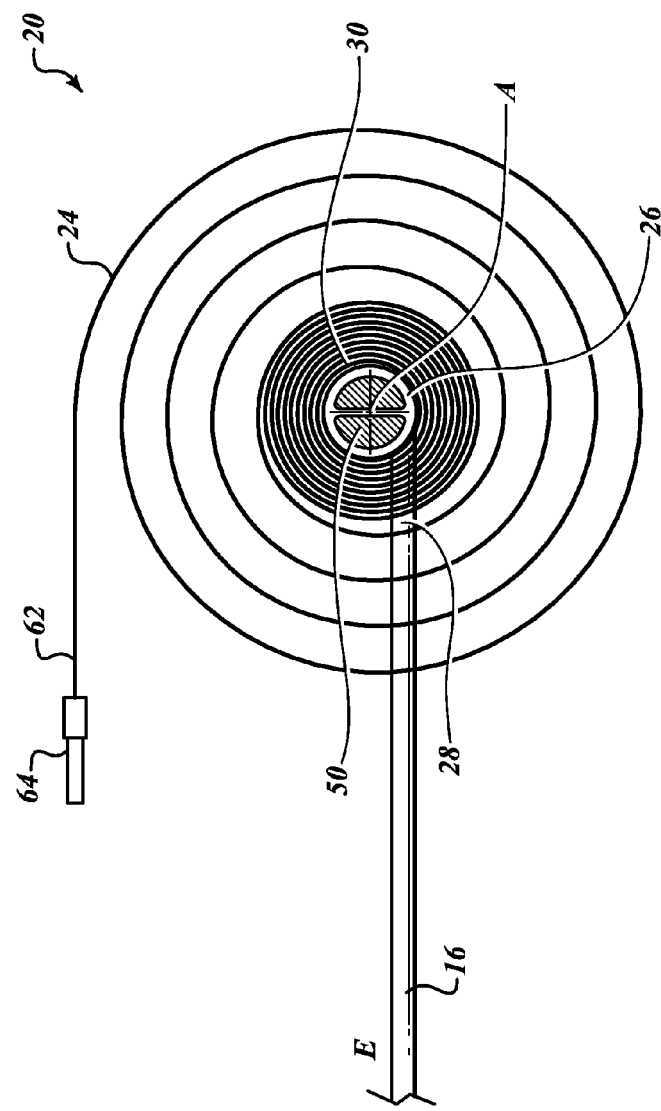
FIG. 7 is a schematic diagram showing a cable and a flexible circuit member of the cable management system of FIG. 2 in a cable extended configuration.

FIGS. 6 and 7 are schematic diagrams illustrating the operation of the cable management system 20 shown in FIG. 2 with portions of the reel 22 and the spring 42 removed for purposes of clarity.

As illustrated in FIG. 6, the first end 28 of the cable 16 and the first end 30 of the flexible circuit member 24 are each physically connected to central shaft 26. Consequently, when the central shaft 26 rotates about the central axis A, the first end 28 of the cable 16 and the first end 30 of the flexible circuit member 24 rotate in unison therewith. A portion of the cable 16 and a portion of the flexible circuit member 24 thus remain relatively fixed with respect to the central shaft 26 and each other throughout rotational movement of the same.

Electrical connection structures are provided within, at, or proximate the central shaft 26 to electrically couple conductors 52 (FIG. 4) of the flexible circuit member 24 to respective wires 56 (FIG. 5) of the cable 16. Such structures may include rigidly mounted electrical connectors or yokes (not shown) wired together in electrical communication on the central shaft 26 to receive corresponding mating connectors or yokes (not shown) of each of the first end 28 of the cable 16 and the first end 30 of the flexible circuit member 24. Alternatively, the wires 56 of the cable 16 and the conductors 52 of the flexible circuit member 24 may be welded, soldered or otherwise coupled together or to electrical terminals or the like on the central shaft 26. Still further, it is appreciated that the wires 56 of the cable 16 may be coupled to the conductors 52 of the flexible circuit member 24 along the central shaft or within a cavity of the same. In any case, a continuous uninterrupted conductive path is maintained between wires 56 of the cable 16 and respective conductors 52 of the flexible circuit member 24. In this manner, a plurality of continuous conductive paths or signal channels are maintained from a terminal end 60 of the cable 16 through the cable 16 to appropriate connections at the central shaft 26 through the flexible circuit member 24 to a terminal end 62 of the same. In some embodiments, one or more of the wires 56 of the cable 16 and/or one or more of the conductors 52 of the flexible circuit member 24 may not be utilized. In such embodiments, the cable 16 may include more or fewer wires 56 than the number of conductors 52 of the flexible circuit member 24.

FIG. 6 illustrates the cable management system 20 in a retracted configuration R with the cable 16 wound tightly in a first direction about the central shaft 26. More particularly, the cable 16 spirals outwardly in the first direction (shown as clockwise) with the first end 28 of the cable 16 coupled to the central shaft 26 and the terminal end 60 coupled to the transducer unit 14. In some embodiments, the terminal end 60 of the cable 16 may include an electrical connector (not shown) for selective attachment of various electrical components. For example, the terminal end 60 of the cable 16 may include a connector to receive interchangeable transducer units 14 that are specifically configured for different applications, such as, for example, gynecology, urology and prostate examinations.

In the retracted position R, the flexible circuit member 24 is likewise wound about the central shaft 26, but in an opposite direction of the cable 16 (shown as counter-clockwise). When in the retracted configuration R, the flexible circuit member 24 is wound about the central shaft 26 such that a substantial portion of the flexible circuit member 24 is located proximate an outer periphery of the cable management system 20, thereby creating a central region that is substantially void. The flexible circuit member 24 is connected at the first end 30 to the central shaft 26 with the terminal end 62 connected to an electrical connector 64 to interface with other electrical components. For example, the electrical connector 64 may be secured to a mating connector on a printed circuit board contained in the control and display unit 12 (FIG. 1) of an ultrasound diagnostic imaging system 10. In this manner, ultrasound data may be gathered via a transducer unit 14 and transmitted to the board for subsequent processing. In some embodiments, the terminal end 62 of the flexible circuit member 24 may be directly connected to a printed circuit board or other component without an intermediate electrical connector 64. The terminal end 62 of the flexible circuit member 24 is secured such that it remains substantially fixed relative to the central axis A during operation.

FIG. 7 illustrates the cable management system 20 in an extended configuration E with the cable 16 unwound from the central shaft 26. In this extended configuration E, the flexible circuit member 24 is wound relatively tightly about the central shaft 26 and fills the central region of the cable management system 20. Accordingly, the flexible circuit member 24 winds progressively tighter to contract about the central shaft 26 as the cable 16 is extended, and thereby compensates or adjusts for revolutions of the central shaft 26 caused by the extending cable 16. As a corollary, the flexible circuit member 24 unwinds, relaxes or loosens from about the central shaft 26 as the cable 16 retracts back from the extended configuration E. The cable management system 20 thus features a seesaw type operational behavior in which the flexible circuit member 24 winds or contracts about the central shaft 26 as the cable 16 is extended and unwinds, loosens or relaxes as the cable 16 is retracted.

While FIGS. 6 and 7 illustrate configurations in which the cable 16 is fully retracted and fully extended, it is appreciated that, according to some embodiments, the cable 16 may be selectively withdrawn and held at intermediate positions between these extreme configurations. In such embodiments, the cable management system 20 may include a lock, latch or other mechanism (not shown), such as, for example, a ratchet and pawl device, to selectively secure the cable 16 at intermediate positions between fully extended and fully retracted. In this manner, the cable management system 20 may allow a user to extend the transducer unit 14 and hence cable 16 to a desired extended length and lock the cable 16 at that length while operating the transducer unit 14. The user can thus collect ultrasound data for subsequent diagnostic purposes without interference from excessive cord lengths that would otherwise be present. The rotatable reel 22 is biased towards the retracted configuration R so that when finished using the transducer unit 14 the user may unlock or unlatch the reel 22 to automatically return the cable 16 to the retracted configuration R.

Although embodiments of the cable management systems 20 disclosed herein have been described in connection with ultrasound diagnostic imaging equipment, it will be apparent to those skilled in the art that these systems and aspects of the same may be applied to a wide range of equipment and devices and are thus by no means limited to ultrasound diagnostic imaging applications. Further, it is appreciated that embodiments of the cable management systems 20 may be designed as modular self contained units for removable attachment to various equipment and devices or may be housed or integrated into the same.

Moreover, aspects of the various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A cable management system, comprising:
an elongated flexible circuit member including a flexible base substrate and a plurality of conductors;
a shaft coupled to an end of the cable and an end of the flexible circuit member, the shaft configured to rotate about a central axis as the cable moves between a generally extended and a generally retracted configuration; and
an elongated cable including a plurality of wires, at least one of the wires of the cable electrically coupled to a conductor of the elongated flexible circuit member, the cable movable between a generally retracted configuration and a generally extended configuration, and wherein, when the cable moves towards the generally extended configuration, the flexible circuit member contracts about the central axis with an end of the flexible circuit member remaining substantially fixed relative to the central axis.

2. The cable management system of claim 1, further comprising:
a spring to bias the cable towards the generally retracted configuration.

3. The cable management system of claim 1 wherein a ratio of a thickness of the cable to a thickness of the flexible circuit member is greater than or equal to 10:1.

4. The cable management system of claim 1 wherein the cable includes at least twenty wires, each wire of the cable electrically coupled to a corresponding one of the conductors of the flexible circuit member.

5. A cable management system, comprising:
a reel rotatable about a central axis, the reel including a central shaft;
an elongated flexible circuit member coupled at one end to the central shaft of the reel, the flexible circuit member including a flexible base substrate and a plurality of conductors; and
an elongated cable including a plurality of wires coupled at one end to the central shaft of the reel, at least one of the wires of the cable electrically coupled to a conductor of the flexible circuit member, wherein the cable is movable between a generally retracted configuration and a generally extended configuration, the flexible circuit member winding about the reel when the cable moves towards the generally extended configuration and unwinding from the reel when the cable moves towards the generally retracted configuration.

6. The cable management system of claim 5, further comprising:
a spring to bias the cable towards the generally retracted configuration.

7. The cable management system of claim 6 wherein the spring includes a first end and a second end, the first end of the spring fixed relative to the central axis and the second end of the spring coupled to the reel to bias the cable towards the generally retracted configuration.

8. The cable management system of claim 5 wherein the reel includes a first channel sized to receive the majority of the cable in the generally retracted configuration and a second channel sized to receive a majority of the flexible circuit member in each of the generally retracted and generally extended configurations.

9. The cable management system of claim 5 wherein a ratio of a thickness of the cable to a thickness of the flexible circuit member is greater than or equal to 10:1.

10. The cable management system of claim 5 wherein the flexible circuit member includes a spring element that biases the cable towards the generally retracted configuration.

11. The cable management system of claim 5 wherein when the cable is in the generally retracted configuration a majority of the flexible circuit member is located proximate an outer periphery of the reel.

12. A cable management system for an ultrasound instrument, comprising:
a reel rotatable about a central axis, the reel including a central shaft;
an elongated flexible circuit member having a flexible base substrate and a plurality of conductors, a first end of the flexible circuit member physically coupled to the central shaft of the reel to rotate in unison therewith;
an elongated cable having a plurality of wires, a first end of the cable physically coupled to the central shaft of the reel to rotate in unison therewith and each of the wires electrically coupled to a respective conductor of the flexible circuit member; and
a transducer unit physically and communicatively coupled to a second end of the cable, the transducer unit movable between a retracted configuration and an extended configuration, the flexible circuit member winding about the central shaft of the reel as the transducer unit moves away from the retracted configuration.

13. The cable management system of claim 12, further comprising:
an electrical connector coupled to a second end of the flexible circuit member to electrically connect the conductors of the flexible circuit member to a control and display unit of the ultrasound instrument, the electrical connector being substantially fixed relative to the central axis of the reel when connected to the control and display unit.

14. The cable management system of claim 12, further comprising: a central pin for rotatably supporting the reel, the central pin fixed relative to a control and display unit of the ultrasound instrument.

15. The cable management system of claim 12, further comprising: a spring to bias the transducer unit towards the retracted position.

16. The cable management system of claim 12 wherein a ratio of a thickness of the cable to a thickness of the flexible circuit member is greater than or equal to 10:1.

17. The cable management system of claim 12 wherein the flexible circuit member includes a spring element that biases the transducer unit towards the retracted position.

18. The cable management system of claim 12 wherein when the cable is in the retracted configuration a majority of the flexible circuit member is located proximate an outer periphery of the reel.

* * * * *